US005569588A

United States Patent [19]
Ashby et al.

[11] Patent Number: 5,569,588
[45] Date of Patent: Oct. 29, 1996

[54] METHODS FOR DRUG SCREENING

[75] Inventors: Matthew Ashby, San Aselmo; Jasper Rine, Moraga, both of Calif.

[73] Assignee: The Regents of the University of California, Oakland, Calif.

[21] Appl. No.: 512,811

[22] Filed: Aug. 9, 1995

[51] Int. Cl.$^6$ .................. C12Q 1/68; C12N 15/00; C07H 21/04
[52] U.S. Cl. .................. 435/6; 435/29; 435/172.1; 536/23.4; 536/24.1
[58] Field of Search .................. 435/6, 172.1, 172.3; 536/23.4, 24.1; 935/23, 47

[56]  References Cited

U.S. PATENT DOCUMENTS

| | | | |
|---|---|---|---|
| 4,981,784 | 1/1991 | Evans et al. | 435/6 |
| 5,378,603 | 1/1995 | Brown et al. | 435/6 |

FOREIGN PATENT DOCUMENTS

| | | |
|---|---|---|
| 92304902.7 | 12/1992 | European Pat. Off. . |
| WO92/05286 | 9/1990 | WIPO . |
| WO94/17208 | 8/1994 | WIPO . |

Primary Examiner—George C. Elliott
Assistant Examiner—John S. Brusca
Attorney, Agent, or Firm—Richard Aron Osman, PH.D.

[57]  ABSTRACT

Methods and compositions for modeling the transcriptional responsiveness of an organism to a candidate drug involve (a) detecting reporter gene product signals from each of a plurality of different, separately isolated cells of a target organism, wherein each cell contains a recombinant construct comprising a reporter gene operatively linked to a different endogenous transcriptional regulatory element of the target organism such that the transcriptional regulatory element regulates the expression of the reporter gene, and the sum of the cells comprises an ensemble of the transcriptional regulatory elements of the organism sufficient to model the transcriptional responsiveness of said organism to a drug; (b) contacting each cell with a candidate drug; (c) detecting reporter gene product signals from each cell; (d) comparing reporter gene product signals from each cell before and after contacting the cell with the candidate drug to obtain a drug response profile which provides a model of the transcriptional responsiveness of said organism to the candidate drug.

8 Claims, No Drawings

METHODS FOR DRUG SCREENING

BACKGROUND

The field of the invention is pharmaceutical drug screening. Pharmaceutical research and development is a multibillion dollar industry. Much of these resources are consumed in efforts to focus the specificity of lead compounds. In addition, many programs are aborted after decades of costly yet fruitless efforts to limit side effects or toxicity of candidate drugs. Accordingly, tools that can abbreviate the research and discovery phase of drug development are desirable. Several in vitro or cell culture-based methods have been described for identifying compounds with a particular biological effect through the activation of a linked reporter. Gadski et al. (1992) EP 92304902.7 describes methods for identifying substances which regulate the synthesis of an apolipoprotein; Evans et al. (1991) U.S. Pat. No. 4,981,784 describes methods for identifying ligand for a receptor and Farr et al. (1994) WO 94/17208 describes methods and kits utilizing stress promoters to determine toxicity of a compound.

In general, the principle that has been applied in the existing pharmaceutical industry for the discovery and development of new lead compounds for drugs has been the establishment of sensitive and reliable in vitro assays for purified enzymes, and then screening large numbers of compounds and culture supernatants for any ability to inhibit enzyme activity. The present invention exploits the recent advances in genome science to provide for the rapid screening of large numbers of compounds against a systemic target comprising substantially all targets in a pathway, organism, etc. for rare compounds having the ability to inhibit the protein of interest. The invention described herein, in effect, turns the drug discovery process inside out. This invention provides information on the mechanism of action of every compound that affects cells, regardless of the target. In addition, the relative specificity of all lead compounds is immediately established.

SUMMARY OF THE INVENTION

The invention provides methods and compositions for estimating the physiological specificity of a candidate drug. In general, the subject methods involve (a) detecting reporter gene product Signals from each of a plurality of different, separately isolated cells of a target organism, wherein each of said cells contains a recombinant construct comprising a reporter gene operatively linked to a different endogenous transcriptional regulatory element (e.g. promoter) of said target organism such that said transcriptional regulatory element regulates the expression of said reporter gene, wherein said plurality of cells comprises an ensemble of the transcriptional regulatory elements of said organism sufficient to model the transcriptional responsiveness of said organism to a drug; (b) contacting each said cell with a candidate drug; (c) detecting reporter gene product signals from each of said cells; (d) comparing said reporter gene product signals from each of said cells before and after contacting each of said cells with said candidate drug to obtain a drug response profile; wherein said drug response profile provides an estimate of the physiological specificity or biological interactions of said candidate drug.

DETAILED DESCRIPTION OF THE INVENTION

The Genome Reporter Matrix.

The invention provides methods and compositions for estimating the physiological specificity of a candidate drug by modeling the transcriptional responses of the target organism with an ensemble of reporters, the expressions of which are regulated by transcription regulatory genetic elements derived from the genome of the target organism. The ensemble of reporting cells comprises as comprehensive a collection of transcription regulatory genetic elements as is conveniently available for the targeted organism so as to most accurately model the systemic transcriptional response. Suitable ensembles generally comprise thousands of individually reporting elements; preferred ensembles are substantially comprehensive, i.e. provide a transcriptional response diversity comparable to that of the target organism. Generally, a substantially comprehensive ensemble requires transcription regulatory genetic elements from at least a majority of the organism's genes, and preferably includes those of all or nearly all of the genes. We term such a substantially comprehensive ensemble a genome reporter matrix.

It is frequently convenient to use an ensemble or genome reporter matrix derived from a lower eukaryote or common animal model to obtain preliminary information on drug specificity in higher eukaryotes, such as humans. Because yeast, such as *Saccharomyces cerevisiae*, is a bona fide eukaryote, there is substantial conservation of biochemical function between yeast and human cells in most pathways, from the sterol biosynthetic pathway to the Ras oncogene. Indeed, the absence of many effective antifungal compounds illustrates how difficult it has been to find therapeutic targets that would selectively kill fungal but not human cells. One example of a shared response pathway is sterol biosynthesis. In human cells, the drug Mevacor (lovastatin) inhibits HMG-CoA reductase, the key regulatory enzyme of the sterol biosynthetic pathway. As a result, the level of a particular regulatory sterol decreases, and the cells respond by increased transcription of the gene encoding the LDL receptor. In yeast, Mevacor also inhibits HMG-CoA reductase and lowers the level of a key regulatory sterol. Yeast cells respond in an analogous fashion to human cells. However, yeast do not have a gene for the LDL receptor. Instead, the same effect is measured by increased transcription of the ERG 10 gene, which encodes acetoacetyl CoA thiolase, an enzyme also involved in sterol synthesis. Thus the regulatory response is conserved between yeast and humans, even though the identity of the responding gene is different.

Advantages of the Genome Reporter Matrix as a Vehicle for Pharmaceutical Development The advantages of the subject methods over prior art screening methods may be illustrated by examples. Consider the difference between an in vitro assay for HMG-CoA reductase inhibitors as presently practiced by the pharmaceutical industry, and an assay for inhibitors of sterol biosynthesis as revealed by the ERG 10 reporter. In the case of the former, information is obtained only for those rare compounds that happen to inhibit this one enzyme. In contrast, in the case of the ERG 10 reporter, any compound that inhibits nearly any of the approximately 35 steps in the sterol biosynthetic pathway will, by lowering the level of intracellular sterols, induce the synthesis of the reporter. Thus, the reporter can detect a much broader range of targets than can the purified enzyme, in this case 35 times more than the in vitro assay.

Drugs often have side effects that are in part due to the lack of target specificity. However, the in vitro assay of HMG-CoA reductase provides no information on the specificity of a compound. In contrast, a genome reporter matrix reveals the spectrum of other genes in the genome also affected by the compound. In considering two different compounds both of which induce the ERG10 reporter, if one compound affects the expression of 5 other reporters and a second compound affects the expression of 50 other reporters, the first compound is, a priori, more likely to have fewer side effects. Because the identity of the reporters is known or determinable, information on other affected reporters is informative as to the nature of the side effect. A panel of reporters can be used to test derivatives of the lead compound to determine which of the derivatives have greater specificity than the first compound.

As another example, consider the case of a compound that does not affect the in vitro assay for HMG-CoA reductase nor induces the expression of the ERG10 reporter. In the traditional approach to drug discovery, a compound that does not inhibit the target being tested provides no useful information. However, a compound having any significant effect on a biological process generally has some consequence on gene expression. A genome reporter matrix can thus provide two different kinds of information for most compounds. In some cases, the identity of reporter genes affected by the inhibitor evidences to how the inhibitor functions. For example, a compound that induces a cAMP-dependent promoter in yeast may affect the activity of the Ras pathway. Even where the compound affects the expression of a set of genes that do not evidence the action of the compound, the matrix provides a comprehensive assessment of the action of the compound that can be stored in a database for later analyses. A library of such matrix response profiles can be continuously investigated, much as the Spectral Compendiums of chemistry are continually referenced in the chemical arts. For example, if the database reveals that compound X alters the expression of gene Y, and a paper is published reporting that the expression of gene Y is sensitive to, for example, the inositol phosphate signaling pathway, compound X is a candidate for modulating the inositol phosphate signaling pathway. In effect the genome reporter matrix is an informational translator that takes information on a gene directly to a compound that may already have been found to affect the expression of that gene. This tool should dramatically shorten the research and discovery phase of drug development, and effectively leverage the value of the publicly available research portfolio on all genes.

In many cases, a drug of interest would work on protein targets whose impact on gene expression would not be known a priori. The genome reporter matrix can nevertheless be used to estimate which genes would be induced or repressed by the drug. In one embodiment, a dominant mutant form of the gene encoding a drug-targeted protein is introduced into all the strains of the genome reporter matrix and the effect of the dominant mutant, which interferes with the gene product's normal function, evaluated for each reporter. This genetic assay informs us which genes would be affected by a drug that has a similar mechanism of action. In many cases, the drug itself could be used to obtain the same information. However, even if the drug itself were not available, genetics can be used to predetermine what its response profile would be in the genome reporter matrix. Furthermore, it is not necessary to know the identity of any of the responding genes. Instead, the genetic control with the dominant mutant sorts the genome into those genes that respond and those that do not. Hence, if drugs that disrupt a given cellular function were desired, dominant mutants for such function introduced into the genome reporter matrix reveal what response profile to expect for such an agent.

For example, taxol, a recent advance in potential breast cancer therapies, has been shown to interfere with tubulin-based cytoskeletal elements. Hence, a dominant mutant form of tubulin provides a response profile informative for breast cancer therapies with similar modes of action to taxol. Specifically, a dominant mutant form of tubulin is introduced into all the strains of the genome reporter matrix and the effect of this dominant mutant, which interferes with the microtubule cytoskeleton, evaluated for each reporter. Thus, any new compound that induces the same response profile as the dominant tubulin mutant would provide a candidate for a taxol-like pharmaceutical.

In addition, the genome reporter matrix can be used to genetically create or model various disease states. In this way, pathways present specifically in the disease state can be targeted. For example, the specific response profile of transforming mutant $Ras2^{val19}$ identifies $Ras2^{val19}$ induced reporters. Here, the matrix, in which each unit contains the $Ras2^{val19}$ mutation is used to screen for compounds that restore the response profile to that of the matrix lacking the mutation.

Though these examples are directed to the development of human therapeutics, informative response profiles can often be obtained in nonhuman reporter matrices. Hence, for disease causing genes with yeast homologs, even if the function of the gene is not known, a dominant form of the gene can be introduced into a yeast-based reporter matrix to identify disease state specific pathways for targeting. For example, a reporter matrix comprising the yeast mutant $Ras2^{val19}$ provides a discovery vehicle for pathways specific to the human analog, the oncogene $Ras2^{val12}$.

Application of Novel Combinatorial Chemistries with the Genome Reporter Matrix.

Among the most important advances in drug development have been advances in combinatorial synthesis of chemical libraries. In conventional drug screening with purified enzyme targets, combinatorial chemistries can often help create new derivatives of a lead compound that will also inhibit the target enzyme but with some different and desirable property. However, conventional methods would fail to recognize a molecule having a substantially divergent specificity. The genome reporter matrix offers a simple solution to recognizing new specificities in combinatorial libraries. Specifically, pools of new compounds are tested as mixtures across the matrix. If the pool has any new activity not present in the original lead compound, new genes are affected among the reporters. The identity of that gene provides a guide to the target of the new compound. Furthermore, the matrix offers an added bonus that compensates for a common weakness in most chemical syntheses. Specifically, most syntheses produce the desired product in greatest abundance and a collection of other related products as contaminants due to side reactions in the synthesis. Traditionally the solution to contaminants is to purify away from them. However, the genome reporter matrix exploits the presence of these contaminants. Syntheses can be adjusted to make them less specific with a greater number of side reactions and more contaminants to determine whether anything in the total synthesis affects the expression of target genes of interest. If there is a component of the mixture with the desired activity on a particular reporter, that reporter can be used to assay purification of the desired component from the mixture. In effect, the reporter matrix allows a focused survey of the effect on single genes to compensate for the impurity of the mixture being tested.

Isoprenoids are a specially attractive class for the genome reporter matrix. In nature, isoprenoids are the champion signaling molecules. Isoprenoids are derivatives of the five carbon compound isoprene, which is made as an intermediate in cholesterol biosynthesis. Isoprenoids include many of the most famous fragrances, pigments, and other biologically active compounds, such as the antifungal sesquiterpenoids, which plants use defensively against fungal infection. There are roughly 10,000 characterized isoprene derivatives and many more potential ones. Because these compounds are used in nature to signal biological processes, they are likely to include some of the best membrane permeant molecules.

Isoprenes possess another characteristic that lends itself well to drug discovery through the genome reporter matrix. Pure isoprenoid compounds can be chemically treated to create a wide mixture of different compounds quickly and easily, due to the particular arrangement of double bonds in the hydrocarbon chains. In effect, isoprenoids can be mutagenized from one form into many different forms much as a wild-type gene can be mutagenized into many different mutants. For example, vitamin D used to fortify milk is produced by ultraviolet irradiation of the isoprene derivative known as ergosterol. New biologically active isoprenoids are generated and analyzed with a genome reporter matrix as follows. First a pure isoprenoid such as limonene is tested to determine its response profile across the matrix. Next, the isoprenoid (e.g. limonene) is chemically altered to create a mixture of different compounds. This mixture is then tested across the matrix. If any new responses are observed, then the mixture has new biologically active species. In addition the identity of the reporter genes provides information regarding what the new active species does, an activity to be used to monitor its purification, etc. This strategy is also applied to other mutable chemical families in addition to isoprenoids.

Applications of the Genome Reporter Matrix in Antibiotic and Antifungal Discovery.

Fungi are important pathogens on plants and animals and make a major impact on the production of many food crops and on animal, including human, health. One major difficulty in the development of antifungal compounds has been the problem of finding pharmaceutical targets in fungi that are specific to the fungus. The genome reporter matrix offers a new tool to solve this problem. Specifically, all molecules that fail to elicit any response in the Saccharomyces reporter are collected into a set, which by definition must be either inactive biologically or have a very high specificity. A reporter library is created from the targeted pathogen such as Cryptococcus, Candida, Aspergillus, Pneumocystis etc. All molecules from the set that do not affect Saccharomyces are tested on the pathogen, and any molecule that elicits an altered response profile in the pathogen in principle identifies a target that is pathogen-specific. As an example, a pathogen may have a novel signaling enzyme, such as an inositol kinase that alters a position on the inositol ring that is not altered in other species. A compound that inhibits that enzyme would affect the signaling pathway in the pathogen, and alter a response profile, but due to the absence of that enzyme in other organisms, would have no effect. By sequencing the reporter genes affected specifically in the target fungus and comparing the sequence with others in Genbank, one can identify biochemical pathways that are unique to the target species. Useful identified products include not only agents that kill the target fungus but also the identification of specific targets in the fungus for other pharmaceutical screening assays.

The identification of compounds that kill bacteria has been successfully pursued by the pharmaceutical industry for decades. It is rather simple to spot a compound that kills bacteria in a spot test on a petri plate. Unfortunately, growth inhibition screens have provided very limited lead compound diversity. However, there is much complexity to bacterial physiology and ecology that could offer an edge to development of combination therapies for bacteria, even for compounds that do not actually kill the bacterial cell. Consider for example the bacteria that invade the urethra and persist there through the elaboration of surface attachments known as timbrae. Antibiotics in the urine stream have limited access to the bacteria because the urine stream is short-lived and infrequent. However, if one could block the synthesis of the timbrae to detach the bacteria, existing therapies would become more effective. Similarly, if the chemotaxis mechanism of bacteria were crippled, the ability of bacteria to establish an effective infection would, in some species, be compromised. A genome reporter matrix for a bacterial pathogen that contains reporters for the expression of genes involved in chemotaxis or fimbrae synthesis, as examples, identifies not only compounds that do kill the bacteria in a spot test, but also those that interfere with key steps in the biology of the pathogen. These compounds would be exceedingly difficult to discover by conventional means.

Applications of Human Cell Based Genome Reporter Matrices.

A genome reporter matrix based on human cells provides many important applications. For example, an interesting application is the development of antiviral compounds. When human cells are infected by a wide range of viruses, the cells respond in a complex way in which only a few of the components have been identified. For example, certain interferons are induced as is a double-stranded RNase. Both of these responses individually provides some measure of protection. A matrix that reports the induction of interferon genes and the double stranded RNase is able to detect compounds that could prophylactically protect cells before the arrival of the virus. Other protective effects may be induced in parallel. The incorporation of a panel of other reporter genes in the matrix is used to identify those compounds with the highest degree of specificity.

Use of the Genome Reporter Matrix.

The procedure to be followed in the subject methods will now be outlined. The initial step involves determining the basal or background response profile by detecting reporter gene product signals from each of a plurality of different, separately isolated cells of a target organism under one or more of a variety of physical conditions, such as temperature and pH, medium, and osmolarity. As discussed above, the target organism may be a yeast, animal model, human, plant, pathogen, etc. Generally, the cells are arranged in a physical matrix such as a microtiter plate. Each of the cells contains a recombinant construct comprising a reporter gene operatively linked to a different endogenous transcriptional regulatory element of said target organism such that said transcriptional regulatory element regulates the expression of said reporter gene. A sufficient number of different recombinant cells are included to provide an ensemble of transcriptional regulatory elements of said organism sufficient to model the transcriptional responsiveness of said organism to a drug. In a preferred embodiment, the matrix is substantially comprehensive for the selected regulatory elements, e.g. essentially all of the gene promoters of the targeted organism are included. Other cis-acting or trans-acting transcription regulatory regions of the targeted organism can also be evaluated. In one embodiment, a genome reporter matrix is constructed from a set of lacZ fusions to a substantially comprehensive set of yeast genes. The fusions are preferably constructed in a diploid cell of the a/a mating type to allow the introduction of dominant mutations by mating, though haploid strains also find use with particularly sensitive reporters for certain functions. The fusions are conveniently arrayed onto a microtiter plate having 96 wells separating distinct fusions into wells having defined alphanumeric X-Y coordinates, where each well (defined as a unit) confines a cell or colony of cells having a construct of a reporter gene operatively joined to a different transcriptional promoter. Permanent collections of these plates are readily maintained at −80° C. and copies of this collection can be made and propagated by simple mechanics and may be automated with commercial robotics.

The methods involve detecting a reporter gene product signal for each cell of the matrix. A wide variety of reporters may be used, with preferred reporters providing conveniently detectable signals (e.g. by spectroscopy). Typically, the signal is a change in one or more electromagnetic properties, particularly optical properties at the unit. As examples, a reporter gene may encode an enzyme which catalyzes a reaction at the unit which alters light absorption properties at the unit, radiolabeled or fluorescent tag-labeled nucleotides can be incorporated into nascent transcripts which are then identified when bound to oligonucleotide probes, etc. Examples include β-galactosidase, invertase, green fluorescent protein, etc. Invertase fusions have the virtue that functional fusions can be selected from complex libraries by the ability of invertase to allow those genes whose expression increases or decreases by measuring the relative growth on medium containing sucrose with or without the compound of interest. Electronic detectors for optical, radiative, etc. signals are commercially available, e.g. automated, multi-well colorimetric detectors, similar to automated ELISA readers. Reporter gene product signals may also be monitored as a function of other variables such as stimulus intensity or duration, time (for dynamic response analyses), etc.

In a preferred embodiment, the basal response profiles are determined through the colorimetric detection of a lacZ reaction product. The optical signal generated at each well is detected and linearly transduced to generate a corresponding digital electrical output signal. The resultant electrical output signals are stored in computer memory as a genome reporter output signal matrix data structure associating each output signal with the coordinates of the corresponding microtiter plate well and the stimulus or drug. This information is indexed against the matrix to form reference response profiles that are used to determine the response of each reporter to any milieu in which a stimulus may be provided.

After establishing a basal response profile for the matrix, each cell is contacted with a candidate drug. The term drug is used loosely to refer to agents which can provoke a specific cellular response. Preferred drugs are pharmaceutical agents, particularly therapeutic agents. The drug induces a complex response pattern of repression, silence and induction across the matrix (i.e. a decrease in reporter activity at some units, an increase at others, and no change at still others). The response profile reflects the cell's transcriptional adjustments to maintain homeostasis in the presence of the drug. While a wide variety of candidate drugs can be evaluated, it is important to adjust the incubation conditions (e.g. concentration, time, etc.) to preclude cellular stress, and hence insure the measurements of pharmaceutically relevant response profiles. Hence, the methods monitor transcriptional changes which the cell uses to maintain cellular homeostasis. Cellular stress may be monitored by any convenient way such as membrane potential (e.g. dye exclusion), cellular morphology, expression of stress response genes, etc. In a preferred embodiment, the compound treatment is performed by transferring a copy of the entire matrix to fresh medium containing the first compound of interest.

After contacting the cells with the candidate drug, the reporter gene product signals from each of said cells is again measured to determine a stimulated response profile. The basal of background response profile is then compared with (e.g. subtracted from, or divided into) the stimulated response profile to identify the cellular response profile to the candidate drug. The cellular response can be characterized in a number of ways. For example, the basal profile can be subtracted from the stimulated profile to yield a net stimulation profile. In another embodiment, the stimulated profile is divided by the basal profile to yield an induction ratio profile. Such comparison profiles provide an estimate of the physiological specificity of the candidate drug.

In another embodiment of the invention, a matrix of hybridization probes corresponding to a predetermined population of genes of the selected organism is used to specifically detect changes in gene transcription which result from exposing the selected organism or cells thereof to a candidate drug. In this embodiment, one or more cells derived from the organism is exposed to the candidate drug in vivo or ex vivo under conditions wherein the drug effects a change in gene transcription in the cell to maintain homeostasis. Thereafter, the gene transcripts, primarily mRNA, of the cell or cells is isolated by conventional means. The isolated transcripts or cDNAs complementary thereto are then contacted with an ordered matrix of hybridization probes, each probe being specific for a different one of the transcripts, under conditions wherein each of the transcripts hybridizes with a corresponding one of the probes to form hybridization pairs. The ordered matrix of probes provides, in aggregate, complements for an ensemble of genes of the organism sufficient to model the transcriptional responsiveness of the organism to a drug. The probes are generally immobilized and arrayed onto a solid substrate such as a microtiter plate. Specific hybridization may be effected, for example, by washing the hybridized matrix with excess non-specific oligonucleotides. A hybridization signal is then detected at each hybridization pair to obtain a matrix-wide signal profile. A wide variety of hybridization signals may be used; conveniently, the cells are pre-labeled with radionucleotides such that the gene transcripts provide a radioactive signal that can be detected in the hybridization pairs. The matrix-wide signal profile of the drug-stimulated cells is then compared with a matrix-wide signal profile of negative control cells to obtain a specific drug response profile.

The invention also provides means for computer-based qualitative analysis of candidate drugs and unknown compounds. A wide variety of reference response profiles may be generated and used in such analyses. For example, the response of a matrix to loss of function of each protein or gene or RNA in the cell is evaluated by introducing a dominant allele of a gene to each reporter cell, and determining the response of the reporter as a function of the mutation. For this purpose, dominant mutations are preferred but other types of mutations can be used. Dominant mutations are created by in vitro mutagenesis of cloned genes followed by screening in diploid cells for dominant mutant alleles.

In an alternative embodiment, the reporter matrix is developed in a strain deficient for the UPF gene function, wherein the majority of nonsense mutations cause a dominant phenotype, allowing dominant mutations to be constructed for any gene. UPF1 encodes a protein that causes the degradation of MRNA's that, due to mutation, contain premature termination codons. In routants lacking UPF1 function most nonsense mutations encode short truncated protein fragments. Many of these interfere with normal protein function and hence have dominant phenotypes. Thus in a upf1 mutant, many nonsense alleles behave as dominant mutations (see, e.g. Leeds, P. et al. (1992) Molec. Cell Biology. 12:2165–77).

The resultant data identify genetic response profiles. These data are sorted by individual gene response to determine the specificity of each gene to a particular stimulus. A weighting matrix is established which weights the signals proportionally to the specificity of the corresponding reporters. The weighting matrix is revised dynamically, incorporating data from every screen. A gene regulation function is then used to construct tables of regulation identifying which cells of the matrix respond to which mutation in an indexed gene, and which mutations affect which cells of the matrix.

Response profiles for an unknown stimulus (e.g. new chemicals, unknown compounds or unknown mixtures) may be analyzed by comparing the new stimulus response profiles with response profiles to known chemical stimuli. Such comparison analyses generally take the form of an indexed report of the matches to the reference chemical response profiles, ranked according to the weighted value of each matching reporter. If there is a match (i.e. perfect score), the response profile identifies a stimulus with the same target as one of the known compounds upon which the response profile database is built. If the response profile is a subset of cells in the matrix stimulated by a known compound, the new compound is a candidate for a molecule with greater specificity than the reference compound. In particular, if the reporters responding uniquely to the reference chemical have a low weighted response value, the new compound is concluded to be of greater specificity. Alternatively, if the reporters responding uniquely to the reference compound have a high weighted response value, the new compound is concluded to be active downstream in the same pathway. If the output overlaps the response profile of a known reference compound, the overlap is sorted by a quantitative evaluation with the weighting matrix to yield common and unique reporters. The unique reporters are then sorted against the regulation tables and best matches used to deduce the candidate target. If the response profile does not either overlap or match a chemical response profile, then the database is inadequate to infer function and the response profile may be added to the reference chemical response profiles.

The response profile of a new chemical stimulus may also be compared to a known genetic response profile for target gene(s). If there is a match between the two response profiles, the target gene or its functional pathway is the presumptive target of the chemical. If the chemical response profile is a subset of a genetic response profile, the target of the drug is downstream of the mutant gene but in the same pathway. If the chemical response profile includes as a subset a genetic response profile, the target of the chemical is deduced to be in the same pathway as the target gene but upstream and/or the chemical affects additional cellular components. If not, the chemical response profile is novel and defines an orphan pathway.

While described in terms of cells comprising reporters under the transcriptional control of endogenous regulatory regions, there are a number of other means of practicing the invention. For example, each unit of a genome reporter matrix reporting on gene expression might confine a different oligonucleotide probe capable of hybridizing with a corresponding different reporter transcript. Alternatively, each unit of a matrix reporting on DNA-protein interaction might confine a cell having a first construct of a reporter gene operatively joined to a targeted transcription factor binding site and a second hybrid construct encoding a transcription activation domain fused to a different structural gene, i.e. a one-dimensional one-hybrid system matrix. Alternatively, each unit of a matrix reporting on protein-protein interactions might confine a cell having a first construct of a reporter gene operatively joined to a targeted transcription factor binding site, a second hybrid construct encoding a transcription activation domain fused to a different constitutionally expressed gene and a third construct encoding a DNA-binding domain fused to yet a different constitutionally expressed gene, i.e. a two-dimensional two-hybrid system matrix.

The following examples are offered by way of illustration and not by way of limitation.

EXAMPLES

1. Transcriptional promoter-reporter gene matrix

A) Construction of a physical matrix stimulated with the drug mevinolin (lovastatin, Meracon).

Mevinolin is a compound known to inhibit cholesterol biosynthesis. Initially, the maximal non-toxic (as measured by cell growth and viability) concentration of mevinolin on the reporter cells was determined by serial dilution to be 25 ug/ml. To produce a mevinolin-stimulated matrix, each well of 60 microtiter plates is filled with 100 ul culture medium containing 25 ug/ml mevinolin in a 2% ethanol solution. An aliquot of each member of the reporter matrix is added to each well allowing for a dilution of approximately 1:100. The cells are incubated in the medium until the turbidity of the average reporter increases by 20 fold. Each well is then quantified for turbidity as a measure of growth, and is treated with a lysis solution to allow measurement of β-galactosidase from each fusion.

B) Generation of an output signal matrix data structure.

Both the turbidity and the B-galactosidase are read on commercially available microtiter plate readers (e.g. Bio-Rad) and the data captured as an ASCII file. From this file, the value of the individual cells in the reporter matrix to a 2% ethanol solution in the reference response profile is subtracted. The difference corresponds to the mevinolin response profile. This file is converted in the computer to a table indexed by the response of each cell to the inhibitor. For example, the genes encoding acetoacetyl-CoA thiolase and squalene synthase increase 10 fold, while SIR3, and LEU2, two unrelated genes, remain unchanged. The response of the reporter matrix to other compounds is similarly determined and stored as output response profiles.

C) Comparison of Signal Matrix data structure with a Signal Matrix database.

A physical matrix is constructed as describe above except the mevinolin is replaced with an unknown test compound. The resultant response profile is compared to the response profiles of a library of known bioactive compounds and analyzed as described above. For example, if the test compound output profile shows both acetoacetyl-CoA thiolase and squalene synthase gene induced, then the output profile matches that expected of an inhibitor of cholesterol synthesis. If the response profile has fewer other cells affected than the response profile to mevinolin, the unknown compound is a candidate for greater specificity. If the response profile of the new chemical affects fewer other reporters than the response profile to mevinolin, and if the other reporters affected by mevinolin have a lower weighted value, then the compound is a candidate for greater specificity. If the response profile has more different cells affected than the response profile to mevinolin, then the compound is a candidate for less specificity. In the case where mixtures of compounds are tested, the highest weighted responses are evaluated to determine whether they can be deconvoluted into the response profile of two different compounds, or of two different genetic response profiles.

2. Reporter transcript-oligonucleotide hybridization probe matrix: Construction of stimulated physical matrix and generation of an output signal matrix data structure.

Unlabeled oligonucleotide hybridization probes complementary to the mRNA transcript of each yeast gene are arrayed on a silicon substrate etched by standard techniques (e.g. Fodor et al. (1991) Science 252, 767). The probes are of length and sequence to ensure specificity for the corresponding yeast gene, typically about 24–240 nucleotides in length.

A confluent HeLa cell culture is treated with 15 ug/ml mevinolin in 2% ethanol for 4 hours while maintained in a humidified 5% $CO_2$ atmosphere at 37° C. Messenger RNA is extracted, reverse transcribed and fluorophore-labeled according to standard methods (Sambrook et al., Molecular Cloning, 3rd ed.). The resultant cDNA is hybridized to the array of probes, the array is washed free of unhybridized labeled cDNA, the hybridization signal at each unit of the array quantified using a confocal microscope scanner (instruments by Molecular Devices and Affymetrix), and the resultant matrix response data stored in digital form.

3. Two-dimensional two-hybrid matrix

A) Construction of stimulated physical matrix.

The two-dimensional two-hybrid (see, e.g. Chien et al. (1991) PNAS, 88, 9578)matrix is designed to screen for compounds that specifically affect the interaction of two proteins, e.g. the interaction of a human signal transducer and activator of transcription (STAT) with an interleukin receptor. Two hybrid fusions are generated by standard methods: each strain contains a portion of the targeted human STAT gene, fused to a portion of a yeast or bacterial gene encoding a DNA binding domain (e.g. GAL4:1–147). The DNA sequence recognized by that DNA binding domain (e.g. $UAS_G$) is inserted in place of the enhancer sequence 5' to the selected reporter (e.g. lacZ). The strain also contains another fusion consisting of an intracellular portion of the targeted receptor gene whose protein product interacts with the STAT. This receptor gene is fused with a gene fragment encoding a transcriptional activation domain (e.g. GAL4:768–881).

B) Generation of signal matrix data structure.

Both the turbidity and the galactosidase are read on commercial microtiter plate readers (BioRad) and the data captured as an ASCII file.

C) Comparison of signal matrix data structure with database.

Data are analyzed for those compounds that block the interaction of the two human proteins by reducing the signal produced from the reporter in the various strains containing pairs of human proteins. The output is processed to identify compounds with a large impact on a reporter whose expression is dependent on a single pair of interacting human proteins. An inverted weighting matrix is used to evaluate these data as preferred compounds do not affect even the least specific reporters in the matrix.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for modeling of the transcriptional responsiveness of an organism to a candidate drug which has an effect on gene transcription in cells of said organism, comprising steps:

(a) detecting reporter gene product signals from each of a plurality of different, separately isolated cells of a target organism, wherein each of said cells contains a recombinant construct comprising a reporter gene operatively linked to a different endogenous transcriptional regulatory element of said target organism such that said transcriptional regulatory element regulates the expression of said reporter gene, wherein said plurality of cells comprises an ensemble of the transcriptional regulatory elements of said organism sufficient to model the transcriptional responsiveness of said organism to a drug;

(b) contacting each of said cells with a candidate drug under conditions wherein said cells maintain homeostasis;

(c) detecting reporter gene product signals from each of said cells;

(d) comparing said reporter gene product signals from each of said cells before and after contacting each of said cells with said candidate drug to obtain a drug response profile;

wherein said drug response profile provides a model of the transcriptional responsiveness of said organism to said candidate drug.

2. A method according to claim 1, said ensemble comprising a majority of all different transcriptional regulatory elements of said organism.

3. A method according to claim 1, said drug being a candidate human therapeutic.

4. A method according to claim 1, wherein said cells are yeast cells.

5. A method according to claim 1, wherein said cells are bacterial cells.

6. A method according to claim 1, wherein said cells are human cells.

7. A method according to claim 1, wherein the reporter gene is the lacZ gene, the suc2 gene, or a gene encoding a green fluorescent protein.

8. A method according to claim 1, wherein said cells are eukaryotic cells.

* * * * *